United States Patent [19]

Rice et al.

[11] Patent Number: Plant 5,393

[45] Date of Patent: Jan. 22, 1985

[54] BOUGAINVILLEA PLANT

[76] Inventors: Jake W. Rice; Patricia A. Rice, both of Box 133, Sutherland Springs, Tex. 78161

[21] Appl. No.: 456,440

[22] Filed: Jan. 7, 1983

[51] Int. Cl.[3] ..... A01H 5/00

[52] U.S. Cl. ..... Plt./54

[58] Field of Search ..... Plt./54

[56] References Cited

PUBLICATIONS

Exotica 4, Graf, 1982, Roehrs Co., E. Rutherford, N. J., pp. 1615 and 2205.

*Primary Examiner*—Robert E. Bagwill

*Attorney, Agent, or Firm*—Cox & Smith Incorporated

[57] ABSTRACT

The present invention relates to a new and distinct variety of Bougainvillea plant which we discovered in Stockdale, Wilsoln County, Texas. The cultivar name of the new Bougainvillea plant is P J Weeping Beauty.

1 Drawing Figure

1

The new plant is a variegated sport of the *B. glabra Sanderiana* variety. This sport is distinguished by its exceptionally fine-stems, small and medium sized leaves, cascading branches, compact growth relative to other varieties of *B. glabra Sanderiana,* with a weeping appearance. The extremely fine stem and the denseness of the foliage leave the lavender bracts as the only common feature between the parent plant and the sport.

The leaves are oval-shaped with definite pointed tips. Some leaves alternate on opposed sides of the stem while other leaves appear directly across from each other. The leaves are one-quarter inch (¼") apart to one inch (1") apart with as many as ten (10) leaves in a two inch (2") space giving an extremely dense and full appearance. The sizes of the leaves range from one-half inch (½")×one and one-half inch (1½") to one and one-quarter inch (1¼")×three inches (3"). The leaves are variegated having a green colored, irregularly-shaped center with cream colored outside edges such that they each exhibit a different pattern.

The stem is extremely fine and varies from a light green color in new growth to a tan color in the old wood. There are fewer thorns than occur on other varieties of *B. glabra Sanderiana* and those that do occur are small and very soft.

Because of the fineness of the stem, a young plant will only grow to a height of approximately four to six inches before bending over and cascading downward. This bending is unlike the upward growth of other, bush-type varieties of *B. glabra.* Due to this downward bending, a five-year old plant will reach a height of only ten to twelve inches. The stem will grow to a length of approximately 24 to 36 inches, and will be approximately four millimeters in diameter at its base and one millimeter in diameter at the tip.

The bloom is one inch (1") long by one-quarter inch (¼") across the top with a lavender throat blending into a cream colored top.

The bracts are lavender, three-quarter inch (¾")×one and one-half inch (1½), oval shaped with pointed tips.

2

THE PLANT

Origin: Sport of Bougainvillea. Botanic classification: *Bougainvillea glabra Sanderiana.*

Form: Vine-like bush

Foliage: Abundant variegated.

Size of leaf: One half inch (½") to one and one-quarter inch (1¼")×three (3) inch.

Shape of leaf: Oval with definite pointed tips.

Size of stem: Four millimeters in diameter at base of stem, one millimeter at tip; twenty-four to thirty-six inches in length.

Color:

*Leaves.*—Green center with cream colored outside edges.

*Bracts.*—Lavender.

*Bloom.*—A lavender throat blending into a cream colored top.

*Bracts.*—Plate 41 K 6.

*Bloom.*—Plate 9 I1.

*Leaves.*—Green plate 24 L 1, plate 9 I 1.

*Stem.*—Plate 22 L 4.

"Dictionary of Color" by Maerz and Paul.

We have asexually reproduced our new Bougainvillea variety for five years and eight generations through rooted cuttings grown by us in our nursery in Stockdale, Wilson County, Texas. The aforementioned characteristics and distinctions come true and are established and transmitted through succeeding propagations.

We claim:

1. A new and distinct variety of Bougainvillea plant, substantially as herein shown and described, characterized particularly as to novelty by its variegated leaves having green centers and cream colored outside edges, lavender throated cream-colored blooms, denseness of leaves, fineness of stems, compact growth, and cascading branches.

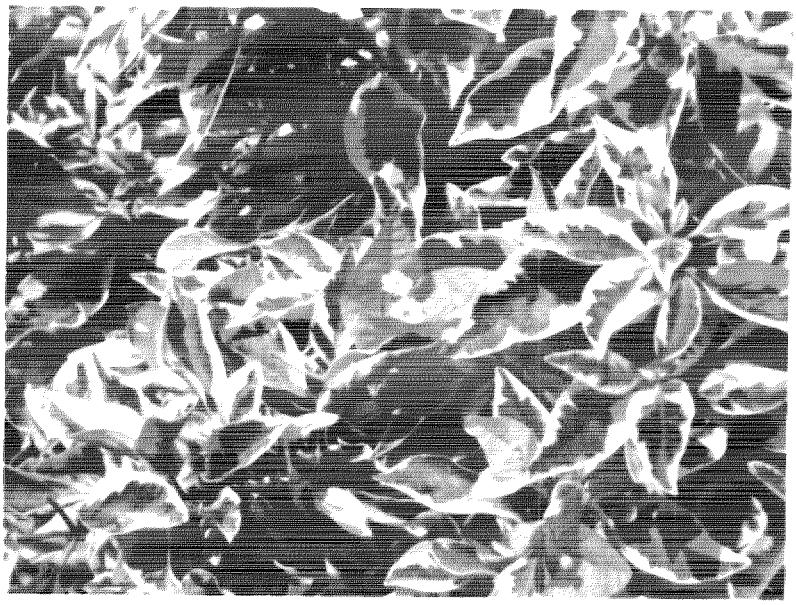

* * * * *